United States Patent [19]
Collica et al.

[11] 4,056,096
[45] Nov. 1, 1977

[54] SHIELDED SYRINGE

[75] Inventors: Carl Collica, New Rochelle; Leonard Epifano, Rye; Ralph Farella, Scarsdale, all of N.Y.

[73] Assignee: Medi-Ray, Inc., Tuckahoe, N.Y.

[21] Appl. No.: 668,531

[22] Filed: Mar. 19, 1976

[51] Int. Cl.$^2$ .............................................. A61B 6/00
[52] U.S. Cl. .................................. 128/1.1; 128/2 A; 250/506
[58] Field of Search ............ 128/1.1, 2 A, 215, 218 P; 250/506, 512, 513, 515

[56] References Cited
U.S. PATENT DOCUMENTS

| | | | |
|---|---|---|---|
| 3,596,659 | 8/1971 | Glasser | 128/215 |
| 3,814,941 | 6/1974 | Czaplinski | 128/1.1 X |
| 3,820,541 | 6/1974 | Langan | 128/215 |
| 3,973,554 | 8/1976 | Tipton | 128/1.1 |

*Primary Examiner*—John D. Yasko
*Attorney, Agent, or Firm*—Martin Novack

[57] ABSTRACT

A shielded syringe suitable for partial disposability. In accordance with the invention there is provided a syringe having a plastic barrel, a tip on the front of the barrel, and a plunger which extends from the rear of the barrel and is manually actuable. The syringe has volumetric indicia disposed in a longitudinal pattern along its barrel. A generally cylindrical body of radiation-shielding material covers the barrel of the syringe. The body has a slot therein which is in registration with at least some of the indicia. A plastic shell of generally cylindrical shape covers the radiation-shielding body and the shell has a slot which is in registration with the slot in the radiation-shielding body. A transparent radiation-shielding member, such as a rectangular leaded-glass member, is proportioned to generally conform in size to the slot in the body and is removably insertible therein. Finally, manually actuable means are provided for retaining the radiation-shielding member in the body. In one embodiment of the invention the retaining means comprises a retaining sleeve proportioned to slideably fit over the shell and which extends over at least a portion of the periphery of the radiation-shielding member so as to retain the radiation-shielding member. In this embodiment the retaining shell has a slot which is in general registration with the parallel edges of the radiation-shielding member, and a pair of lipped panels extend outwardly from the parallel edges of the slot. The lipped panels are proportioned such that the lips engage the upper edges of the radiation-shielding member so as to retain it in place. In another embodiment of the invention the radiation-shielding member is removably slideable within the panels of the shell for temporary retention. Further disclosed is a syringe plunger having a protective shielding plug.

27 Claims, 8 Drawing Figures

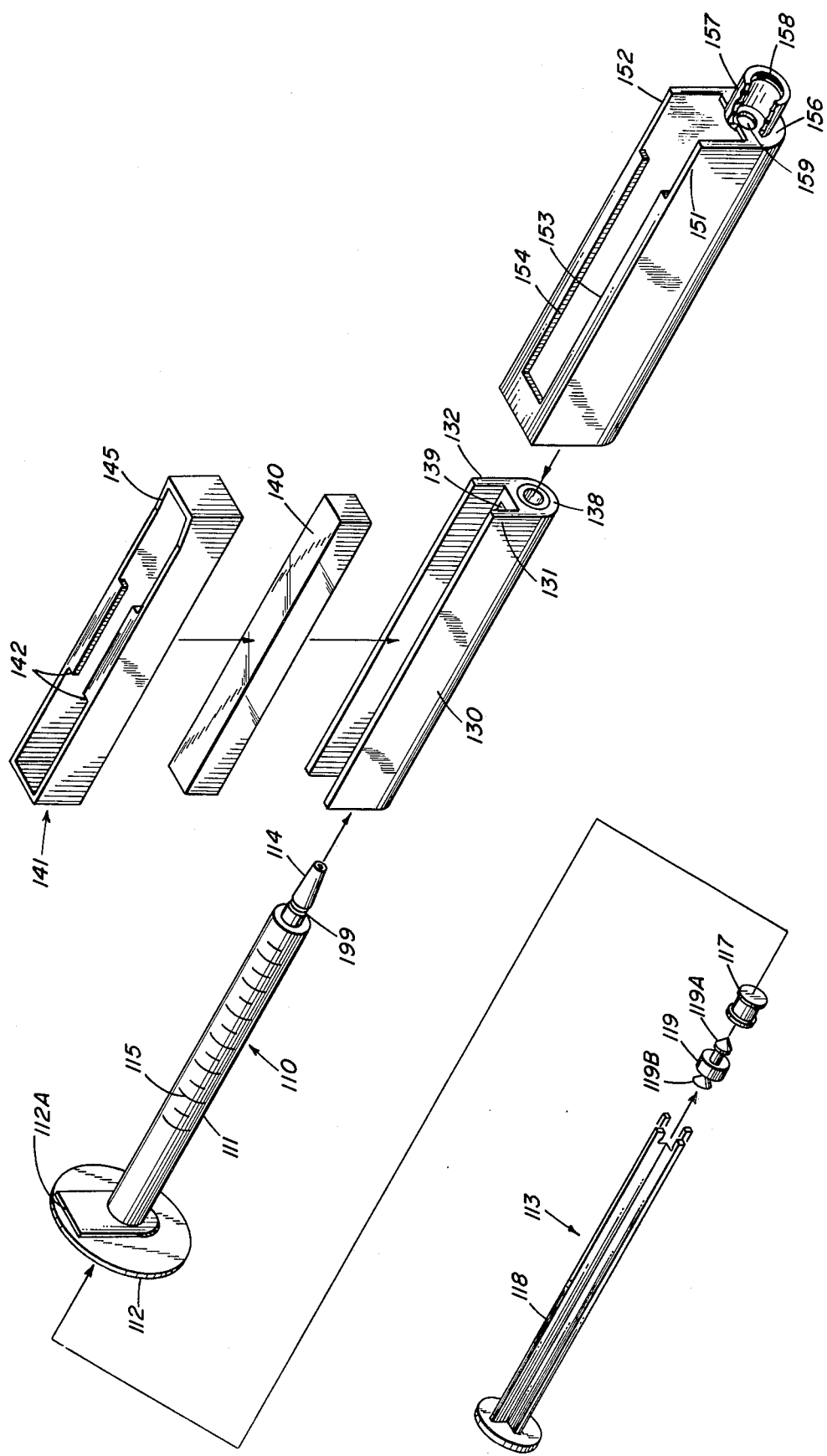

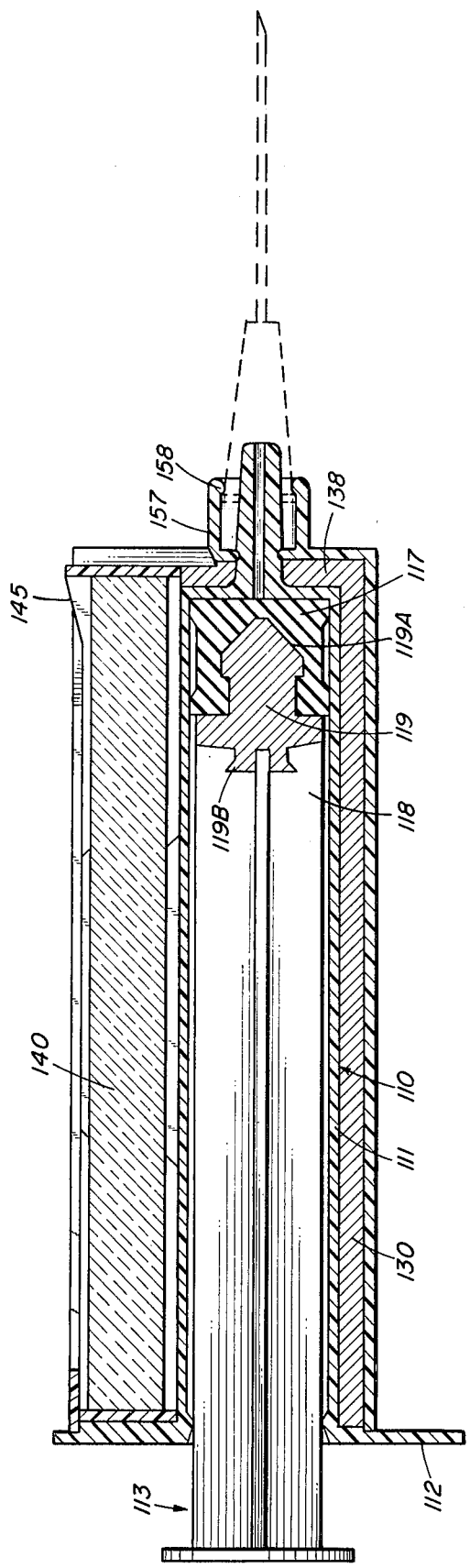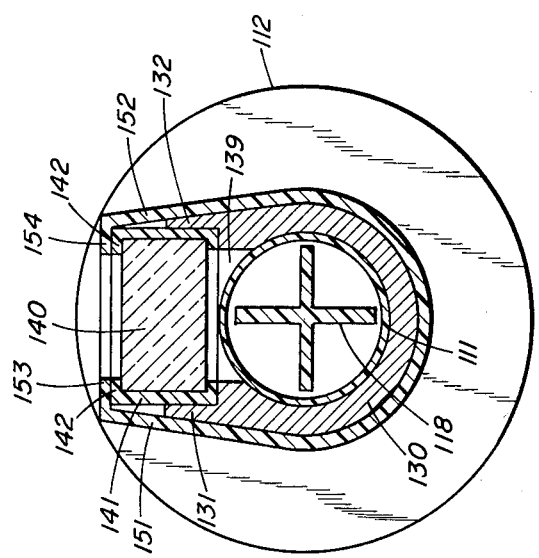

SHIELDED SYRINGE

BACKGROUND OF THE INVENTION

This invention relates to the field of shielding radioactive materials and, more particularly, to an improved syringe shield which is partially disposable.

The subject matter of this invention relates to subject matter disclosed in the copending application Ser. No. 668,532 entitled "Syringe Shield," filed of even date herewith and assigned to the same assignee as the present application.

For various types of diagnostic testing it is necessary to inject radioactive materials into a patient. It is well recognized that technicians who handle these materials need protection against the perils of cumulative ionizing radiation exposure, so provision is commonly made for shielding the materials until such time as they are injected into the patient. Toward this end, various types of syringe shields have been developed. The typical prior art syringe shield includes a lead cylinder which fits over a syringe, the lead body having a window of leaded glass which allows the operator to see the scale on the syringe which is placed within the lead cylinder.

There are a number of disadvantages associated with commercially available syringe shield designs. Some units have a simple cylindrical casing which does not provide adequate shielding forwardly or rearwardly of the syringe length. A further problem is that there is not standardization of syringe sizes, and even syringes having the same volume often have different physical dimensions. For example, a 10 cc syringe may have various possible diameters depending on the particular manufacturer. Thus, special provision is generally necessary to fit a syringe shield to the different possible syringe sizes. For example, in one prior art design the syringe shield is provided with a "set screw" which adjustably protrudes into the syringe shield's bore and engages the syringe so that it cannot move around within the syringe shield. The use of this technique involves some inconvenience and can occasionally cause breakage of the syringe.

Disposable syringes are in widespread use and their advantages are well recognized. Similar advantages would accrue if a disposable shielded syringe existed. For example, a disposable shielded syringe would eliminate the need for medical personnel to locate an appropriately sized syringe shield and assemble the syringe shield over the syringe to be used. The need to decontaminate, clean and maintain permanent syringe shields would also be eliminated. However, to applicant's knowledge no disposable shielded syringe has become commercially available. One reason for this void is the cost of a shielded syringe which includes such expensive parts as a leaded glass window. A further item of expense relates to the need for making shielded syringes suitable for use under hospital or laboratory sanitary conditions. The presence of a heavy shielding body, typically lead, is problematic in that an unfinished lead exterior tends to become dirty and contaminated and is unsuitable for hospital conditions. Provisions for special finishing or plating generally involves expense. As a result of these factors, the prospect of disposing of a syringe shield or of an integrally shielded syringe has not been commercially feasible.

It is an object of this invention to provide a solution to the prior art problems as set forth.

SUMMARY OF THE INVENTION

The present invention is directed to a shielded syringe suitable for partial disposability. In accordance with the invention there is provided a syringe having a plastic barrel, a tip on the front of the barrel, and a plunger slideable in the barrel and extending from the rear of the barrel for manual actuation. The syringe has volumetric indicia disposed in a longitudinal pattern along its barrel. A generally cylindrical body of radiation-shielding material substantially covers the barrel of the syringe. The body has a slot therein which is in registration with at least some of the indicia. A plastic shell of generally cylindrical shape substantially covers the radiation-shielding body and the shell has a slot which is in registration with the slot in the radiation-shielding body. An optically transparent radiation-shielding member, such as a rectangular leaded-glass member, is proportioned to generally conform in size to the slot in the body and is removably insertible therein. Finally, manually actuable means are provided and adapted for engaging the shell and the transparent radiation-shielding member so as to removably retain the transparent radiation-shielding member in the body.

In one embodiment of the invention the retaining means comprises a retaining sleeve proportioned to slideably fit over the shell and which extends over at least a portion of the periphery of the transparent radiation-shielding member so as to retain the member. In this embodiment the retaining sleeve has a slot which is in general registration with the parallel edges of the transparent radiation-shielding member, and a pair of lipped panels extend outwardly from the parallel edges of the slot. The lipped panels are proportioned such that the lips engage the upper edges of the transparent radiation-shielding member so as to retain it in place. In another embodiment of the invention the shell has a pair of lipped panels extending outwardly therefrom and the transparent radiation-shielding member is removably slideable within the panels for temporary retention. In a still further embodiment of the invention the retaining means comprises an apertured cap member mounted on a "living hinge."

In operation, the transparent radiation-shielding member is reuseable and the remainder of the device, which is relatively inexpensive to manufacture, is disposable. The transparent radiation-shielding member can also be temporarily removed in order to assay the radioactive material within the syringe without unnecessarily exposing medical personnel.

In accordance with a further feature of the invention the syringe plunger has a tip within the barrel, a stem coupled to the plunger tip, and a plug of radiation-shielding material mounted rearwardly of the plunger tip. The plug conforms generally in shape to the inner surface of the barrel. The plug serves to shield an operator against radiation emitted axially from the rear of the barrel.

Further features and advantages of the invention will become more readily apparent from the following detailed description when taken in conjunction with the accompanying drawings.

BRIEF DESCRIPTION OF THE DRAWINGS

FIG. 5 is an exploded view of the shielded syringe of FIG. 4.

FIG. 6 is a cross-sectional view as taken through a section defined by arrows 6—6 of FIG. 4.

FIG. 7 is a cross-sectional view as taken through a section defined by arrows 7—7 of FIG. 4.

DESCRIPTION OF THE PREFERRED EMBODIMENT

Figure 1:
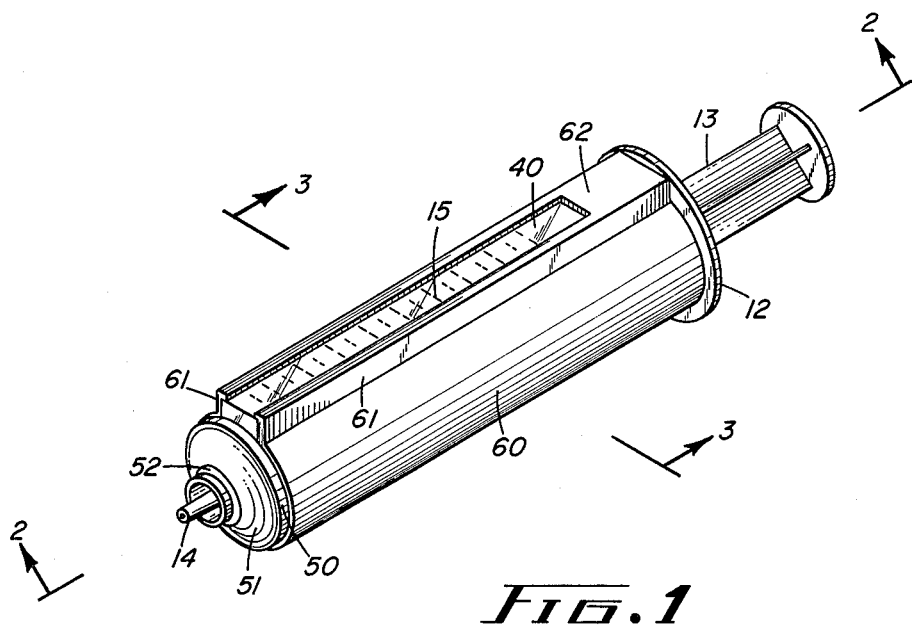
FIG. 1 is an elevational perspective view showing a shielded syringe in accordance with one embodiment of the invention.
Figure 2:
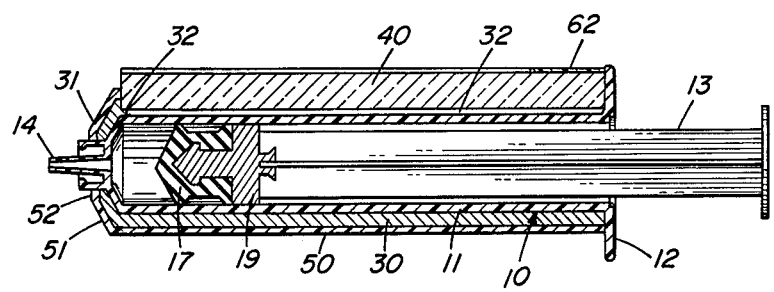
FIG. 2 is a cross-sectional view as taken through a section defined by arrows 2—2 of FIG. 1.
Figure 3:
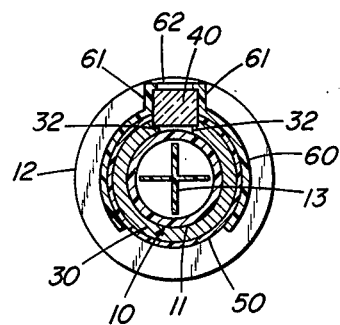
FIG. 3 is a cross-sectional view as taken through a section defined by arrows 3—3 of FIG. 1.
Figure 4:
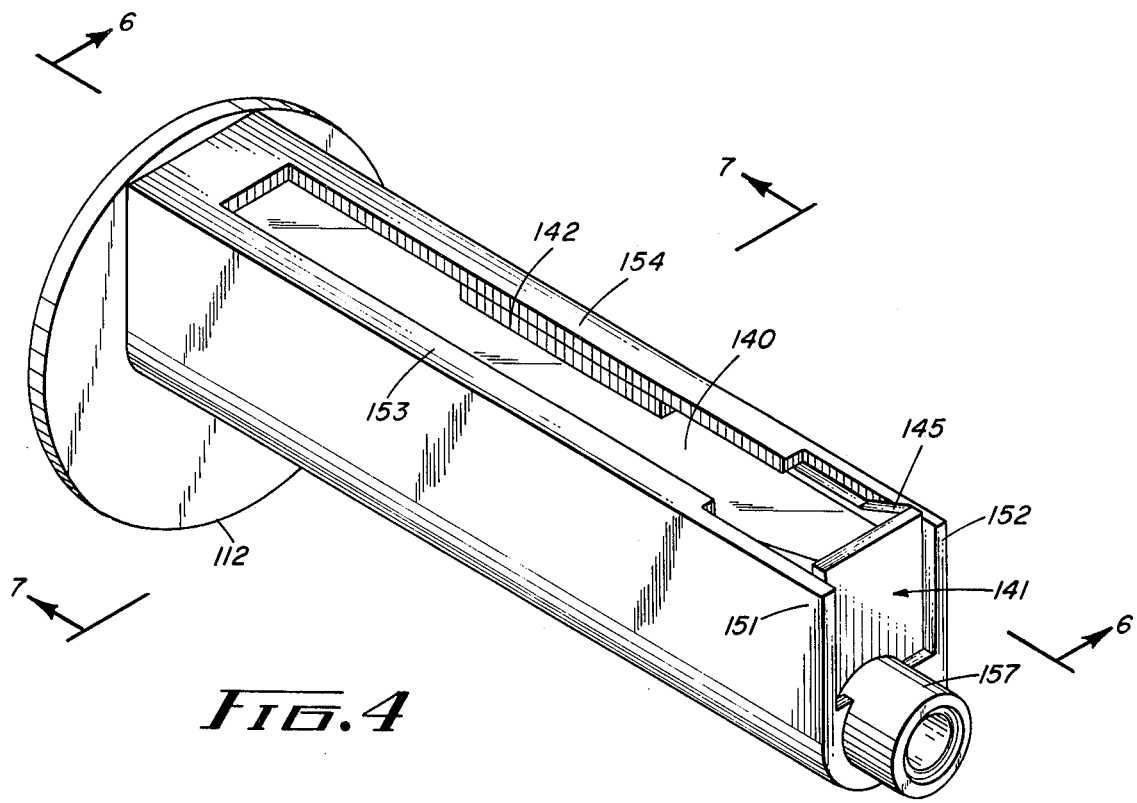
FIG. 4 is an elevational perspective view showing a shielded syringe in accordance with another embodiment of the invention.

Referring to FIGS. 1-3, there is shown a shielded syringe in accordance with an embodiment of the invention. The device core includes the basic elements of a conventional disposable-type plastic syringe, as labeled in the drawings by reference numeral 10. The syringe 10 has a plastic body or barrel 11, a rear flange 12, a plunger 13 and a tip 14. The plunger 13 has a head 17 which is coupled to the plunger stem 18 by a shielding plug 19. This structure is described in detail hereinbelow in conjunction with another embodiment. The syringe body has volumetric indicia disposed in a longitudinal pattern along its barrel as shown at 15. A cylindrical body 30 is formed of a high density radiation-shielding material, such as lead. The body 30, which is open-ended at its rear end and tapers at its front end at 31, is proportioned such that its inner surface conforms generally to the outer surface of the syringe barrel 11. The body 30 has an elongated rectangular slot extending along one side thereof, the slot being in registration with the indicia 15 on the barrel 11. The slot in the body has a flat depression 32 formed around the periphery thereof in which an optically transparent radiation-shielding member 40 is seated. The member 40 is of elongated rectangular shape and may be formed of leaded glass typically having a thickness which is substantially greater than that of the body 30. Thus, the shielding provided by the leaded glass, which is generally of less dense material than lead, will be comparable to the shielding provided by body 30, due to the greater thickness of the leaded glass.

A cylindrical shell 50 is preferably fomed of a rigid plastic material and conforms generally in shape to the outer surface of the shielding body 30. The shell 50 tapers inwardly at the front thereof (at 51) and has a collar 52 which joins the tapered front of the syringe barrel 11. The shell 50 has an elongated rectangular slot which is in registration with the slot in the body 30.

A retaining sleeve 60, also formed of a rigid plastic material, is generally cylidrical in shape and proportioned to slideably fit over the shell 50 from the front end of the device. In the present embodiment, the sleeve 60 has a cross-section which is somewhat greater than semicircular to insure its retention on the device. It will be appreciated, however, that the sleeve could be a full cylinder. The sleeve 60 has a pair of lipped panels 61 which are joined at the rear by connecting panel 62 and which extend outwardly and over the edges of the transparent shieldingg member 40 so as to retain the member in place. The sleeve is preferably slightly tapered toward the front thereof to lightly grip the front of shell 50 so that it won't slip off the shell.

The shielded syringe of the present invention is well suited for use as a disposable item. For example, a number of the described units, each minus the transparent shielding member 40, could be packaged together along with a single transparent shielding member 40. When a shielded syringe is needed, a disposable unit can be taken from the package and the reuseable member 40 inserted in the particular unit by removing the sleeve 60, inserting the transparent shielding member 40, and replacing the sleeve 60. The device is then utilized in the manner of a conventional shielded syringe. After use, the reusable member 40 is extracted by removing the sleeve 61 and the remainder of the device can be disposed of. A further advantage of the device is that the shielding member 40 can be removed at any time during use to assay the radioactive material in the shielded syringe. This is accomplished by removing the member 40 and positioning the exposed aperture toward a detector. In this manner, an assay can be performed without unnecessary exposure of personnel or inconvenience.

Referring to FIGS. 4-7, there is illustrated another embodiment of a shielded syringe device in accordance with the invention. The device includes a syringe 110 having a plastic body or barrel 111, a rear flange 112, a plunger 113, and a tip 114. The plunger 113 has a conventional head or tip 117, typically formed of rubber, which is coupled to a plunger stem 118 by a novel shielding plug 119. The plug 119 is formed of a high density radiation-shielding material, such as lead or tantalum or plated lead. The plug has a cylindrical central portion which conforms generally to the inner circumference of the barrel 111, a front retaining nub 119A which is inserted in an aperture in the rear of tip 117, and a rear retaining nub 119B which snaps into and seats in the front end of the plunger stem 118. The plug 119 serves to shield the operator using the device against radiation emitted axially from the rear of the barrel. This radiation, which would typically and dangerously be directed toward the body of the operator, is generally not satisfactorily shielded in the prior art.

The syringe body has volumetric indicia disposed in a longitudinal pattern along its barrel as shown at 115. A generally cylindrical body 130 is formed of a radiation-shielding material, such as lead, and, as in the previous embodiment, is proportioned such that its inner surface conforms generally to the outer surface of the syringe barrel 111. The body 130 tapers inwardly at its front end at 138 and has an elongated rectangular slot 139 extending along one side thereof, the slot being in registration with the indicia 115 on the barrel 111. The surface containing the slot is flat on top and a pair of panels 131 and 132, which can be formed integrally of the same radiation-shielding material such as lead, are spaced slightly from the parallel edge of the slot and extend outwardly from the flat surface.

A transparent radiation-shielding member 140 is of elongated rectangular shape and may be formed of leaded glass typically having a thickness which is substantially greater than that of the body 130. The member 140 is encased in a rectangular casing 141 which is opened at the top and bottom thereof. Pairs of lips 142 and 143 retain the member 140 within the casing 141. The top edge of the casing slants upward at the front thereof as shown at 145 so that the front end protrudes slightly above the top of the encased member 140. In the present embodiment the casing 141 is formed of material such as rigid plastic and the member 140 is snapped into the casing 141 for permanent retention therein and reuse in a manner to be described. The casing is proportioned to slideably fit within the panels 131 and 132 of body 130 such that the transparent shielding member 140 overlays the periphery of the slot 139 in body 130.

A shell 150 is preferably formed of rigid plastic and is proportioned to generally conform in shape to the outer surface of the body 130. Specifically, the shell 150 has a pair of side panels 151 and 152 which cover and extend above the body panels 131 and 132, respectively. The panels 151 and 152 have lips 153 and 154, respectively, which define an elongated slot that is in registration with the slot 139 in body 130. The front end of the shell 150 is about half opened and has an approximately semicircular wall 156 having a circular aperture 159 therein which receives the tip 114 of the syringe 110. The tip 114 is provided with an annular groove 199 which is retained in aperture 159. A cylindrical shroud 157 extends axially from the wall 156 and protrudes slightly above the top edge of the wall. The shroud 157, which may typically be formed integrally with the body, has an annular protrusion at 158.

To assemble the disposable portion of the device, the syringe 110, with its plunger in place, is inserted into the body 130. The syringe flange 112 has a wall member 112A formed on the inner surface thereof which serves as a spacer between the rear end of the body 130 and the flange. The syringe and body are then inserted into the open-ended rear of the shell. The rear edge of the shell fits over the periphery of wall 119 and is secured to the flange 112 by any suitable means, such as an epoxy bond. This assembly comprises the portion of the shielded syringe which is most suitable for disposability.

In operation, the encased transparent shielding member 140 is inserted in the shell through the front opening therein and is retained from sliding out during use by the protruding portion of the shroud 157. After use, the reusable encased member 140 is removed, removal being facilitated by the raised edge of the casing (145) which can be grasped such as by using the thumb and finger. The casing also provides protection against chipping of the leaded glass. As previously noted, a safe assay is readily achieved with the member 140 removed. The encased transparent shielding member 140 is then typically stored with the package of disposble units until the next use is required.

FIG. 6 shows the manner in which a standard needle can be mounted over the syringe tip and is conveniently retained within the shroud 157 by the annular protrusion 158. This eliminates the need for screwing in the needle and facilitates more convenient operation. However, it will be understood that a standard needle mounting, such as a Luer-lock mounting, can be employed in conjunction with other features of the invention.

Figure 8:
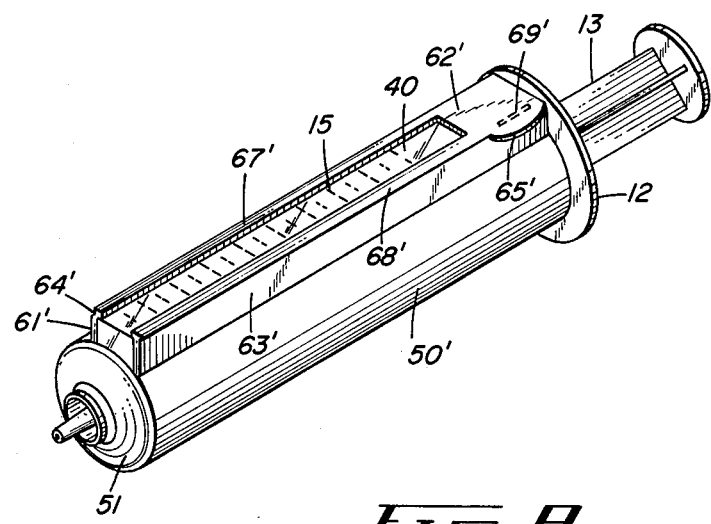
FIG. 8 is an elevational perspective view showing a shielded syringe in accordance with another embodiment of the invention.

The invention has been described with reference to particular embodiments, but it will be appreciated that variations within the spirit and scope of the invention will occur to those skilled in the art. For example, in FIG. 8 there is shown a further embodiment of the invention which is described, for ease of illustration, as a modification of the embodiment of FIG. 1. In the embodiment of FIG. 8 the plastic shell which covers the shielding body 30 (see e.g. FIGS. 2 and 3) is designated by reference numeral 50'. The shell 50' has a pair of outwardly extending panels 61' and 63'. A retaining "cap", comprising a pair of elongated retaining lips 67' and 68' joined at the rear by a connecting panel 62', is coupled to the panel 61' by a "living hinge" at 64', the cap being integrally formed with the panel 61' during molding. The underside of retaining lip 68' has a thin elongated protrusion 69' (shown in dashed line) which snaps into a thin slot in the top of panel 63'. In operation, the transparent shielding member 40 can be inserted from above with the cap swung back and then retained in place. A small flange 65' is provided to facilitate lifting the cap to extricate the member 40.

The present invention is particularly suitable for packaging a "unit dose" of radioactive material. A precalibrated dosage would be loaded into the shielded syringe which may have, for example, a removable inexpensive shielding insert (e.g. formed of lead) to cover the slot 139 during shipping. The user would receive a sterile precalibrated syringe, substitute the transparent radiation-shielding member (if desired) as described above, use the shielded syringe, and then dispose of it, saving the transparent member. The need for a troublesome and hazardous transfer of radioactive material from a shipping container to a syringe is thereby eliminated, thereby decreasing exposure risk. Also, relatively large amounts of isotopes would not have to be ordered by the user to provide adequate reserves in the event of unexpectedly high usage rate.

We claim:

1. A shielded syringe, comprising:
    a syringe having a barrel, a tip on the front of said barrel, and a plunger slideable in said barrel and extending from the rear of said barrel for manual actuation, said syringe having volumetric indicia disposed along its barrel;
    a body of radiation-shielding material substantially covering the barrel of said syringe, said body having a slot therein which is in registration with at least some of said indicia;
    a shell substantially covering said radiation-shielding body, said shell having a slot therein which is in registration with the slot in said radiation-shielding body;
    an optically transparent radiation-shielding member proportioned to generally conform in size to the slot in said body and removably insertible therein; and
    manually actuable means adapted for engaging said shell and said transparent radiation-shielding member so as to removably retain said member in said body.

2. The shielded syringe as defined by claim 1 wherein said barrel and said shell are formed of plastic.

3. The shielded syringe as defined by claim 1 wherein said retaining means comprises a retaining sleeve proportioned to slideably fit over said shell and extending over at least a portion of the periphery of said transparent radiation-shielding member so as to retain said member.

4. The shielded syringe as defined by claim 2 wherein said retaining means comprises a retaining sleeve proportioned to slideably fit over said shell and extending over at least a portion of the periphery of said transparent radiation-shielding member so as to retain said member.

5. The shielded syringe as defined by claim 3 wherein said retaining sleeve has a slot therein which is in registration with parallel edges of said transparent radiation-shielding member, said retaining shell having a pair of lipped panels extending outwardly from the parallel edges of the slot therein.

6. The shielded syringe as defined by claim 5 wherein said outwardly extending lipped panels are proportioned such that the lips engage the upper edges of said transparent radiation-shielding member so as to retain said member.

7. The shielded syringe as defined by claim 1 wherein said plunger has a tip within said barrel, a stem coupled to said plunger tip and a plug of radiation-shielding material mounted rearwardly of said plunger tip, said plug conforming generally in shape to the inner surface of said barrel.

8. The shielded syringe as defined by claim 2 wherein said plunger has a tip within said barrel, a stem coupled to said plunger tip and a plug of radiation-shielding material mounted rearwardly of said plunger tip, said plug conforming generally in shape to the inner surface of said barrel.

9. The shielded syringe as defined by claim 3 wherein said plunger has a tip within said barrel, a stem coupled to said plunger tip and a plug of radiation-shielding material mounted rearwardly of said plunger tip, said plug conforming generally in shape to the inner surface of said barrel.

10. The shielded syringe as defined by claim 1 wherein said shell has a pair of lipped panels extending outwardly therefrom and wherein said transparent radiation-shielding member is removably slideable within said panels for temporary retention.

11. The shielded syringe as defined by claim 2 wherein said shell has a pair of lipped panels extending outwardly therefrom and wherein said transparent radiation-shielding member is removably slideable within said panels for temporary retention.

12. The shielded syringe as defined by claim 11 further comprising a generally rectangular casing proportioned to encase said member, said casing being removably slideable within said panel for temporary retention.

13. The shielded syringe as defined by claim 1 wherein said body has a pair of generally parallel panels extending outwardly therefrom to removably receive said transparent radiation-shielding member.

14. The shielded syringe as defined by claim 13 wherein said shell has a pair of parallel lipped panels extending outwardly adjacent the panels of said body.

15. The shielded syringe as defined by claim 13 further comprising a generally rectangular casing proportioned to encase said transparent radiation-shielding member, said casing being removably slideable within said panels for temporary retention.

16. The shielded syringe as defined by claim 10 wherein said plunger has a tip within said barrel, a stem coupled to said plunger tip and a plug of radiation-shielding material mounted rearwardly of said plunger tip, said plug conforming generally in shape to the inner surface of said barrel.

17. The shielded syringe as defined by claim 14 wherein said plunger has a tip within said barrel, a stem coupled to said plunger tip and a plug of radiation-shielding material mounted rearwardly of said plunger tip, said plug conforming generally in shape to the inner surface of said barrel.

18. The shielded syringe as defined by claim 1 wherein said shell has a pair of panels extending outwardly therefrom and wherein said manually actuable means comprises an aperatured cap member hinged on one of said panels.

19. The shielded syringe as defined by claim 18 wherein said barrel and said shell are formed of plastic.

20. The shielded syringe as defined by claim 19 wherein said cap member is integrally formed on said one panel by a living hinge.

21. The shielded syringe as defined by claim 18 wherein said plunger has a tip within said barrel, a stem coupled to said plunger tip and a plug of radiation-shielding material mounted rearwardly of said plunger tip, said plug conforming generally in shape to the inner surface of said barrel.

22. The shielded syringe as defined by claim 20 wherein said plunger has a tip within said barrel, a stem coupled to said plunger tip and a plug of radiation-shielding material mounted rearwardly of said plunger tip, said plug conforming generally in shape to the inner surface of said barrel.

23. A shielded syringe, comprising:
a syringe having a barrel, a tip on the front of said barrel, and a plunger slideable in said barrel and extending from the rear of said barrel for manual activation;
said plunger having a tip within said barrel, a stem coupled to said plunger tip, and a plug of radiation-shielding material mounted rearwardly of said plunger tip, said plug conforming generally in shape to the inner surface of said barrel; and
a body of radiation-shielding material substantially covering the barrel of said syringe.

24. The shielded syringe as defined by claim 23 wherein said syringe barrel is formed of plastic.

25. The shielded syringe as defined by claim 23 wherein said syringe has volumetric indicia disposed along its barrel and wherein said body has a slot therein which is in registration with at least some of said indicia; further comprising a transparent radiation-shielding member in proportion to generally conform in size to the slot in said body.

26. The shielded syringe as defined by claim 25 further comprising a shell covering said radiation-shielding body, said shell having a slot therein which is in registration with the slot in said radiation-shielding body; and further comprising manually actuable means adapted for engaging said shell and said transparent radiation-shielding member so as to removably retain said member in said body.

27. The shielded syringe as defined by claim 26 wherein said syringe and said shell are formed of plastic.

* * * * *